United States Patent [19]
McCauley

[11] 3,934,464
[45] Jan. 27, 1976

[54] PIPE RING TEST MACHINE
[75] Inventor: Claudius R. McCauley, Covington, La.
[73] Assignee: Apache Corporation, Minneapolis, Minn.
[22] Filed: Aug. 6, 1974
[21] Appl. No.: 495,241

[52] U.S. Cl. .................................................. 73/95
[51] Int. Cl.² ........................ G01N 3/08; G01N 3/28
[58] Field of Search .......... 73/88, 95, 102, 103, 120

[56] References Cited
UNITED STATES PATENTS

| | | | |
|---|---|---|---|
| 1,066,826 | 7/1913 | Lewis | 33/125 R X |
| 1,816,695 | 7/1931 | Pope | 33/125 R |
| 2,318,530 | 5/1943 | Schick et al. | 73/95 |
| 3,039,299 | 6/1962 | Roof | 73/102 X |
| 3,286,512 | 11/1966 | Jagger et al. | 73/88 |

FOREIGN PATENTS OR APPLICATIONS

| | | | |
|---|---|---|---|
| 1,172,366 | 10/1958 | France | 73/95 |
| 219,278 | 8/1968 | U.S.S.R. | 73/95 |

*Primary Examiner*—Harry N. Haroian
*Attorney, Agent, or Firm*—Williamson, Bains & Moore

[57] ABSTRACT

A machine for testing the tensile properties of sections of pipe or tubing, incorporating a split post, with the post halves being displaceable relative to each other to apply a predetermined tensile stress to a ring segment cut from a length of pipe and placed over the split post. Pairs of removable, semicircular shoe discs sized to fit around the post and having different outside diameters may be selectively utilized on the post to test a wide range of sizes of pipe segments.

6 Claims, 5 Drawing Figures

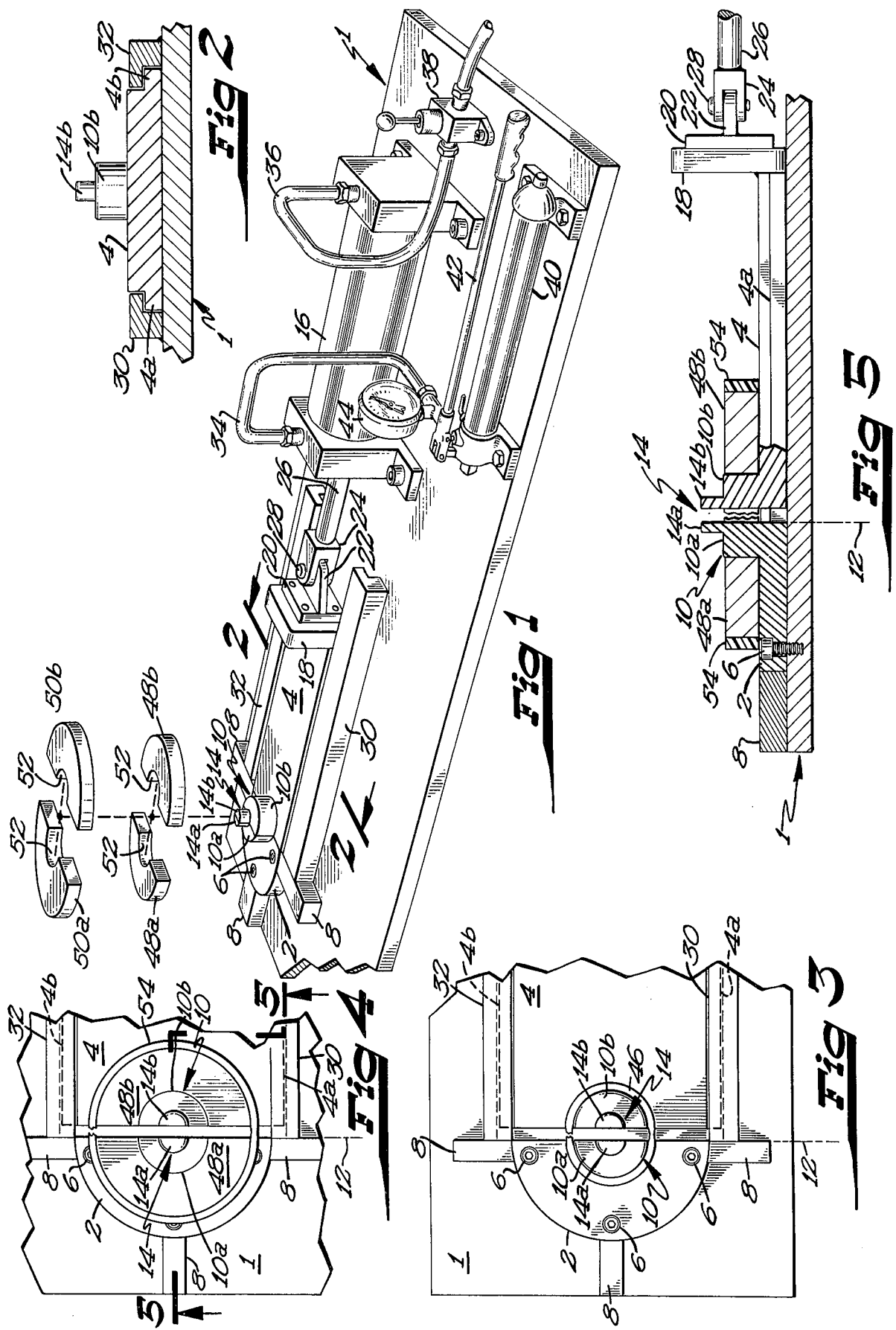

PIPE RING TEST MACHINE

BACKGROUND OF THE INVENTION

Various test methods are known and in use for testing the bursting strength and tensile properties of pipe sections. One such method for testing plastic pipe involves the use of water pressure applied to a closed end pipe section and is satisfactory for testing relatively small pipe on the order of 4 inches in diameter or less. However, this so-called quick burst test procedure is quite cumbersome and costly and entails a considerable waste of material when utilized to test larger diameter plastic pipe. Split disc test methods for applying tensile stress to a pipe ring segment by pulling the disc halves apart are also known. See, for example, American Society for Testing and Materials (ASTM) Publication Designation D2513-68, accepted July 16, 1968, originally published in 1966; and ASTM Publication Designation D2290-69, current edition effective Nov. 14, 1969, originally issued in 1964. The latter type of test method does not lend itself to the testing of large pipe ring segments of different diameters.

Having in mind the foregoing disadvantages and short-comings associated with known methods of testing pipe, I have developed a pipe ring test machine which can be efficiently utilized for testing segments of plastic pipe ranging in size from one inch up through at least 24 inches in diameter.

BRIEF SUMMARY OF THE INVENTION

The pipe ring testing machine of this invention is particularly characterized by a split post mounting fixture which can be quickly and easily utilized in such a way as to apply a predetermined tensile stress to a wide range of sizes of pipe ring segments so as to yield essentially the same results as previously achieved with quick burst pressure tests, but without the concomitant costly equipment and waste of pipe material.

These basic advantages and objectives are achieved by supporting a round post, split along a parting line, in an upright position on a test bed with the two half post segments securely mounted in a substantially horizontal plane on separate base plates movable relative to each other along a displacement line extending substantially perpendicular to the post parting line. Preferably, one of the post segment base plates is stationary and the other is movable back and forth along the displacement line by a power cylinder to which it is attached. A test ring segment cut from a pipe section of predetermined diameter corresponding to that of the split post may be readily placed over the upright split post and supported on the separate base plates. The power cylinder is utilized to shift the movable base plate and one post segment away from the stationary base plate and post segment, and thereby impose a predetermined tensile stress on the test ring segment.

A particularly advantageous feature of my improved pipe ring testing machine resides in the selective utilization of pairs of removable, semicircular shoe discs of different outside diameters around the split posts, on top of the aforesaid base plates, to permit the testing of pipe ring segments of different diameters, larger than that of the split post.

As a further beneficial aspect of my pipe ring tester, I provide an upright stub post segment of semicircular shape affixed to the top end of each of the aforesaid split post segments. These two stub post segments define together an upper, round stub post of lesser diameter than that of the split post on which relatively small pipe ring segments down to 1 inch in diameter may be placed and subjected to a tensile test.

These and other objects and advantages of my invention will become readily apparent as the following description is read in conjunction with the accompanying drawings wherein like reference numerals have been used to designate like elements throughout the several views.

BRIEF DESCRIPTION OF THE DRAWINGS

FIG. 1 is a front, perspective view of the pipe ring test machine of this invention;

FIG. 2 is a vertical section view through a portion of the test machine taken along lines 2—2 of FIG. 1;

FIG. 3 is a fragmentary, top plan view of the test ring segment support portion of the machine shown in FIG. 1;

FIG. 4 is a top plan view of the test machine, similar to FIG. 3, and showing the removable disc arrangement utilized for testing relatively large diameter pipe ring segments; and FIG. 5 is a vertical section view of the test machine setup of FIG. 4 taken along lines 5—5 thereof.

DESCRIPTION OF THE PREFERRED EMBODIMENTS

Referring now to the drawings, I have shown in FIG. 1 a preferred embodiment of the pipe ring test machine of this invention. The machine is mounted on a test bed generally indicated by reference numeral 1. At one end of test bed 1 is an assembly for supporting and mounting a pipe ring segment to be tested. This assembly is comprised of mounting means in the form of a pair of separate, base plates 2 and 4. For reasons hereinafter explained, base plate 2 is stationary, and is secured to test bed 1 by a plurality of hold-down bolts 6. Three retention blocks 8 radially disposed around the periphery of semicircular base plate 2 serve to positively restrain it against displacement under the stress imposed during a testing operation.

Mounted on base plates 2 and 4 is a post 10 split along a parting line 12 which is clearly shown in FIGS. 3 and 4. Split post 10 is comprised of two half post segments 10a and 10b. These two post segments are displaceable relative to each other by virtue of their being affixed to relatively shiftable base plates 2 and 4. As noted above, base plate 2 is preferably stationary, and post segment 10a is permanently affixed thereto. Post segment 10b is permanently affixed to the forward end of movable base plate 4. Post segments 10a and 10b can be formed integrally with their respective base plates 2 and 4 by casting these separate assemblies, or, if desired, the assemblies of post segment 10a and base plate 2 and post segment 10b and base plate 4 can be fabricated by welding and machining. To facilitate the ease of placement of a pipe ring test segment on split post 10, it is preferably disposed in the upright, free standing position shown in FIG. 1 with post segments 10a and 10 b lying in a substantially horizontal plane. As is noted below with respect to the description of the method of use and operation of the test machine, base plates 2 and 4, which abut along split post parting line 12, also extend in a horizontal plane and serve as a rest surface on which components of the test apparatus as well as test ring segments of pipe may be placed.

For reasons hereinafter explained, a pair of upright stub post segments 14a and 14b of semicircular shape project upwardly from the top of each of the split post segments 10a and 10b. These stub post segments are affixed to, or formed integrally with, split post segments 10a and 10b and defined together in their abutting relationship shown in FIG. 1 an upper, stub post 14 of lesser diameter than split post 10 on which pipe ring segments of small diameter may be mounted for testing.

Movable base plate 4 is connected to power actuating means, which preferably takes the form of a pressure operated power cylinder 16, for movement towards and away from stationary base plate 2. This is preferably accomplished by means of an upright connecting plate 18 positioned on the opposite end of base plate 4 from movable post segment 10b and connected to a coupling plate 20. A connector tongue 22 projecting horizontally from the rear face of coupling plate 20 is attached to the bifurcated end 24 of the piston 26 of hydraulic cylinder 16 by means of a connecting pin 28. Base plate 4 is slidably displaceable along a linear path, back and forth with respect to stationary base plate 2 by means of power cylinders 16. In order to ensure that base plate 4 will follow a straight, predetermined displacement line substantially at right angles to parting line 12 of split post 10, it is made in the form of an elongated, rectangular plate which, as shown in FIG. 1, is movable by cylinder 6 along its longitudinal axis. A pair or elongated guide rails or tracks 30 and 32 bear against the opposite, longitudinal sides of movable base plate 4 and restrain it against lateral displacement. Preferably, as is shown most clearly in FIG. 2, guide rails 30 and 32 are of L-shape and overlap the top face of horizontally projecting shoulders 4a and 4b along the side extremities of base plate 4. Guide rails 30 and 32 thereby serve to restrain base plate 4 against vertical displacement, as well as against lateral displacement, and to hold it along its predetermined displacement line at right angles to split post parting line 12 as it is pulled rearwardly by pressure cylinder 16 during a testing operation on a ring segment of pipe.

Power cylinder 16 is preferably of the double acting type, and has flexible hose lines 34 and 36 connected to its opposite ends for conveying actuating fluid to and from the opposite ends of cylinder 16 in a well known manner. A three-way control valve 38 is connected in fluid line 36 for directing pressurized fluid, such as air or hydraulic liquid, to the rear end of cylinder 16. Valve 38 is hand operated, and has a spring return to a neutral position so that at all times when operated by hand the right or rear end of the hydraulic cylinder 16 is open to the atmosphere. This is, of course, the case when pressurized air is utilized as the actuating fluid through lines 36 to shift piston 26 to the left, and to close split post segments 10a and 10b in abutting relation with each other after a test operation had been completed.

Fluid line 34 is connected to pump means for actuating piston 26 to the right for the purpose of pulling post segments 10a and 10b apart during a test operation. Although various types of pump devices may be utilized, including a motor-driven, variable output hydraulic pump, I have shown a hand pump 40, which has proven to be satisfactory. Operating lever 42 on hand pump 40 is utilized to pump hydraulic fluid under pressure through line 34 into the left or forward end of hydraulic cylinder 16. A pressure gauge 44 having a maximum pressure indicator pointer is connected in fluid line 34 to show the maximum pressure obtained during a particular test.

In operation a pump bypass valve (not shown) which is provided with commercially available hand pump 40, is opened and air valve 38 is actuated to introduce pressurized air through line 36 into the right or rear end of cylinder 16. This will cause piston 26 to shift to the left and urge movable base plate 4 and post segment 10b mounted thereon to a closed position in abutting engagement with stationary base plate 2 and stationary post segment 10a. A ring segment cut from a section of pipe to be tested is then placed around split post 10 on top of base plates 2 and 4. Split post 10 is preferably sized to accommodate the testing of pipe ring segments having an internal diameter of 3 inches. If a pipe of this size is to be tested, the test ring segment 46 is placed directly around split post 10 as illustrated in FIG. 3. The maximum reading indicator hand on pressure gauge 44 is then returned to zero, and the bypass valve on pump 40 is closed. The operator then starts pumping lever 42 at a rate such that the test ring 46 will fail in an elapsed time of between 1 and 2 minutes. As piston 26 moves to the right by the application of pressurized fluid through line 34 to cylinder 16, it will pull split post segment 10b away from stationary post segment 10a to an open, separated position along the predetermined displacement line at right angles to parting line 12 of split post 10. As split post segment 10b moves away from its closed position of abutment against stationary post segment 10a, tensile stress will be imposed on pipe ring segment 46. FIG. 3 shows test ring 46 at the instant where its yield point has been reached, and it is being pulled apart. At this point, movable post segment 14b has been pulled to the right by power cylinder 16 in the direction indicated by the arrow in FIG. 3, and separated from stationary post segment 14a.

In the practical use of this test machine, the minimum allowable pressure reading for a particular size and type of pipe is calculated in advance. The machine operator passes or rejects the pipe ring segment tested based on whether or not it yields under tensile stress at this predetermined, minimum pressure. It should be noted that this method of testing is actually more severe than burst tests because of the small bending moment placed on the pipe ring segment at the point where the post segments 10a and 10b separate along parting line 12. In actual practice, a pipe line in service has these additional stresses because of earth loads on the pipe and bending stresses in the line. Therefore, this ring test machine more adequately resembles actual conditions than the quick burst test heretofore utilized.

FIGS. 1, 4 and 5 illustrate the manner in which the test machine of this invention may be utilized to test pipe ring segments having a larger diameter than that of split post 10. This is accomplished by the use of pairs of semicircular shoe discs which may be removably placed around split post 10. Two pairs of such removable discs 48a, 48b and 50a, 50b are shown in exploded view above split post 10 in FIG. 1. A number of pairs of such shoe discs are provided, each having a different outside diameter to accommodate a particular large diameter pipe segment. Each of these pairs of discs has an inner, semicircular recess 52 of a diameter substantially equal to that of split post 10, whereby such removable discs may be snuggly fitted around split post 10. Such a pair of discs having an outside diameter substantially equal to the inside diameter of a particular large pipe segment to be tested is selected and placed around split post segments 10a and 10b on top of base plates 2 and 4 in the manner shown in FIGS. 4 and 5. It will thus be noted that base plates 2 and 4 serve to support removable shoe discs 48a, 48b, as well as to support test ring segments fitted around split post 10. A particular pair of removable shoe discs such as those designated 48a and 48b are placed around split post 10 in the aforesaid manner, with their inner ends abutting each other along parting line 12 of split post 10. A particular ring segment cut from a section of pipe to be tested, having an internal diameter corresponding to the outer diameter of shoe discs 48a and 48b is placed on top of base plates 2 and 4 around discs 48a and 48b as illustrated in FIGS. 4 and 5. This is of course accomplished with movable base plate 4 actuated to its closed position in abutting contact with stationary base plate 2 by means of power cylinder 16. Power cylinder 16 is then utilized in the same manner described above to impart a predetermined tensile stress to a relatively large test ring segment 54 resting on base plates 2 and 4 around removable discs 48a and 48b. Thus, different pairs of removable discs may be selectively utilized on split post 10 to test a wide range of sizes of pipe ring segments greater in diameter than split post 10.

Upper, split stub post 14 may be utilized for testing pipe ring segments having a diameter less than that of split post 10. Upper stub post segments 14a and 14b are sized to provide a small, split stub post 14 on the order of 1 inch in diameter. Pipe segments of such a size may be directly fitted around split post 14 on top of the upper face of larger diameter, split post 10. Removable shoe discs similar to that illustrated at 48a, 48b and 50a, 50b, but having outside diameters in a size range between that of split posts 10 and 14 may be utilized around split post 14 on top of post 10 to test pipe segments having a size range between that of posts 10 and 14. Such removable discs are also notched or recessed to fit snuggly around upper stub post 14.

In actual use, a hinged cover will be provided on top of test bed 1 to cover the entire test apparatus illustrated for safety purposes. For reasons of clarity, no such cover has been shown.

It is to be noted that the clevis type of connection 22, 24, 28 between piston 26 and movable base plate 4 advantageously functions as a flexible coupling. The relative pivotal movement permitted between coupling plate 20 and piston end 24 about coupling pin 28 insures that any misalignment between plate 4 and hydraulic cylinder piston 26 will not result in binding of any portion of the slide mechanism. This would cause an erroneous reading on pressure gauge 44. The use of a flexible coupling such as the clevis connection disclosed herein to connect movable plate 4 to piston 26 provides full freedom of movement of piston 26 through its full stroke without any binding.

I anticipate that the test machine described herein will find particularly widespread application for testing plastic pipe, which is extruded in sizes as great as 24 inches in diameter. Base plates 2 and 4 are sized to accommodate removable shoe discs ranging in size from slightly over 3 inches up to 24 inches in outer diameter.

Those skilled in the art will appreciate that the testing machine disclosed herein can be quickly and effectively used to test a wide range of sizes of pipe segments ranging from very small diameters, up to diameters as large as 24 inches without undue cost and waste of pipe material. I anticipate that various changes may be made in the size, shape and arrangement of the various components of my test machine without departing from the spirit and scope of my invention as defined by the following claims.

What is claimed is:

1. A test machine for simulating a burst pressure test and applying tensile stress to a ring segment cut from a pipe section comprising:

a round post split along a parting line to define two half post segments;

stationary mounting means to which a stationary one of said post segments is rigidly affixed;

movable mounting means to which the other, movable one of said post segments is affixed, said movable mounting means being connected to power actuating means for movement towards and away from said stationary post segment along a displacement line substantially perpendicular to said parting line, said movable post segment being shiftable with said movable mounting means between a closed position abutting against said stationary post segment and an open, extended position displaced therefrom by operation of said power actuating means, whereby a ring segment cut from a pipe section of predetermined diameter may be placed around said split post with said movable post segment in said closed position and subjected to tensile stress by moving said movable post segment towards said open position along said displacement line; and said split post being in a free, upstanding position with said half post segments lying in a substantially horizontal plane, whereby a pipe ring segment to be tested may be readily placed over the top of said split post around said post segments; and a pair of semicircular shoe discs removably placed around said split post on said base plates in abutting contact with each other along said split post parting line, each of said shoe discs having an inner, semicircular recess of a diameter substantially equal to that of said split post, whereby said shoe discs will fit snuggly around said split post, and each of said shoe discs having an outer diameter substantially equal to that of a particular pipe ring segment to be tested, whereby such shoe discs of varying outer diameters may be removably placed on said split post to permit the testing of a wide range of sizes of pipe ring segments greater in diameter than said split post.

2. A test machine for simulating a burst pressure test and applying tensile stress to a ring segment cut from a pipe section comprising:

a round post split along a parting line to define two half post segments;

stationary mounting means to which a stationary one of said post segments is rigidly affixed;

movable mounting means to which the other, movable one of said post segments is affixed, said movable mounting means being connected to power actuating means for movement towards and away from said stationary post segment along a displacement line substantially perpendicular to said parting line, said movable post segment being shiftable with said movable mounting means between a closed position abutting against said stationary post segment and an open, extended position displaced therefrom by operation of said power actuating means, whereby a ring segment cut from a pipe section of predetermined diameter may be placed around said split post with said movable post segment in said closed position and subjected to tensile stress by moving said movable post segment towards said open position along said displacement line; and said split post being in a free, upstanding position with said half post segments lying in a substantially horizontal plane, whereby a pipe ring segment to be tested may be readily placed over the top of said split post around said post segments; and an upright stub post segment of semicircular shape projecting upwardly from the top of each of said split post segments and affixed thereto, said stub post segments defining together in the closed position of said movable post segment an upper stub post of lesser diameter than said split post on which pipe ring segments of lesser diameter than said split post may be placed and tested, the upper face of said split post serving as a rest surface for such lesser diameter test ring segments.

3. A test machine for applying a tensile stress to a ring segment cut from a pipe section comprising:
a round, upright post split along a parting line to define two half post segments, said post segments being affixed to separate, horizontally oriented base plates movable relative to each other along a predetermined displacement line for displacing said post segments from a closed position wherein they abut against each other to an open, separated position;
power actuating means for separating said base plates and said post segments affixed thereto;
a pair of semicircular, shoe discs removably placed around said split post on top of said base plates in abutting contact with each other along said split post parting line, each of said shoe discs having an inner, semicircular recess of a diameter substantially equal to that of said split post, whereby said shoe discs will fit snuggly around said split post, and each of said shoe discs having an outer diameter substantially equal to that of a particular pipe ring segment to be tested, whereby such shoe discs of varying outer diameters may be removably placed on said split post to permit the testing of a wide range of sizes of pipe ring segments greater in diameter than said split post.

4. A pipe ring test machine as defined in claim 3 wherein:
an upright stub post segment of semicircular shape projects upwardly from the top of each of said split post segments and is affixed thereto, said stub post segments defining together in the closed position of said split post segments an upper stub post of lesser diameter than said split on which pipe ring segments of lesser diameter than said split post may be placed and tested, the upper face of said split post serving as a rest surface for such lesser diameter test ring segments.

5. A pipe ring test machine as defined in claim 3 wherein:
one of said post segments is permanently affixed to a stationary base plate, and the other one of said post segments is affixed to a movable base plate attached to a fluid pressure actuated cylinder operable as said power actuating means to pull said other post segment away from said one stationary post segment along said predetermined displacement line.

6. A pipe ring test machine as defined in claim 5 wherein:
said movable base plate is attached to said cylinder by means of a flexible coupling having a vertically extending connecting element defining a pivotal axis about which said movable base plate and said cylinder are free to pivot relative to each other in a horizontal plane.

* * * * *